United States Patent
Liao et al.

(10) Patent No.: US 7,270,284 B2
(45) Date of Patent: Sep. 18, 2007

(54) TISSUE HOMOGENIZER

(75) Inventors: Chun-Jen Liao, Taipei (TW);
Hua-Chun Hsu, Jhunan Township, Miaoli County (TW); Ko-Chun Hsu, Kaohsiung (TW); Da-Pan Chen, Hsinchu (TW); Mei-Chiao Lin, Taisi Township, Yunlin County (TW)

(73) Assignee: Industrial Technology Research Institute, Hsinchu (TW)

( * ) Notice: Subject to any disclaimer, the term of this patent is extended or adjusted under 35 U.S.C. 154(b) by 598 days.

(21) Appl. No.: 10/879,863

(22) Filed: Jun. 29, 2004

(65) Prior Publication Data
US 2005/0139704 A1   Jun. 30, 2005

(30) Foreign Application Priority Data
Dec. 31, 2003   (TW) .............................. 92137613 A

(51) Int. Cl.
*B02C 19/00*   (2006.01)
(52) U.S. Cl. ................... 241/69; 241/2; 241/282.1
(58) Field of Classification Search ............... 241/2, 241/199.12, 277, 282.1, 282.2, 100, 169.1, 241/69
See application file for complete search history.

(56) References Cited

U.S. PATENT DOCUMENTS 3,666,187 A * 5/1972 Norris ..................... 241/89.4
4,828,395 A * 5/1989 Saito et al. ................ 366/143
5,731,199 A * 3/1998 Roggero .................. 435/306.1

* cited by examiner

*Primary Examiner*—Mark Rosenbaum
(74) *Attorney, Agent, or Firm*—Thomas, Kayden, Horstemeyer & Risley

(57) ABSTRACT

A tissue homogenizer. The tissue homogenizer comprises a first chamber, a pair of blades, a first filter and a second filter. The first chamber has a first opening and a second opening. The blades are disposed in the first chamber. The first filter is disposed in the first chamber between the first opening and the blades. The second filter is disposed in the first chamber between the second opening and the blades. A tissue piece is placed between the first filter and the second filter cut by the blade, and moved by a fluid through the second filter to generate homogenized tissue pieces.

11 Claims, 4 Drawing Sheets

TISSUE HOMOGENIZER

BACKGROUND OF THE INVENTION

1. Field of the Invention

The present invention relates to a tissue homogenizer and in particular to a tissue homogenizer for homogenizing live histiocyte.

2. Description of the Related Art

In conventional culture preparation, a tissue piece is cut in a culture dish by scalpel blade, soaked in protease enzyme to separate cells from cytoplasm, and applied to a culture experiment. When cut by scalpel blade, however, the tissue piece is easily polluted and difficult to collect. This conventional method of cutting tissue (homogenizing) wasteful; and when primary tissue is limited, may prevent successful culture.

U.S. Pat. No. 4,874,137 teaches homogenization of tissue piece by ultrasonic wave. U.S. Pat. No. 4,509,695 teaches homogenization of tissue which is originally cooled by liquid nitrogen and then pulverized. U.S. Pat. Nos. 5,829,696, 5,533,683, 4,525,395 and 4,509,695 teach homogenization of tissue piece by pulverizing. The methods mentioned above can damage histiocytes. As well, the degree of homogenization is controlled by an operator creating inconsistent result.

SUMMARY OF THE INVENTION

The present invention comprises a first chamber, a pair of blades, a first filter and a second filter. The first chamber has a first opening and a second opening. The blades are disposed in the first chamber. The first filter is disposed in the first chamber between the first opening and the blades. The second filter is disposed in the first chamber between the second opening and the blades. A tissue piece is placed between the first filter and the second filter for cutting by the blade and a fluid moves the cut tissue pieces through the second filter for homogenization.

The present invention successively cuts, filters, and collects finally the homogenized tissue pieces in a sealed device. The present invention produces homogenized tissue pieces at lower cost in a shorter time, and prevents tissue waste. As well, because the present invention homogenizes the tissue piece by cutting, histiocytes are undamaged and can be applied in live histiocyte culture. Additionally, the present invention provides precise control of homogenized tissue piece by size the filter.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Figure 1:
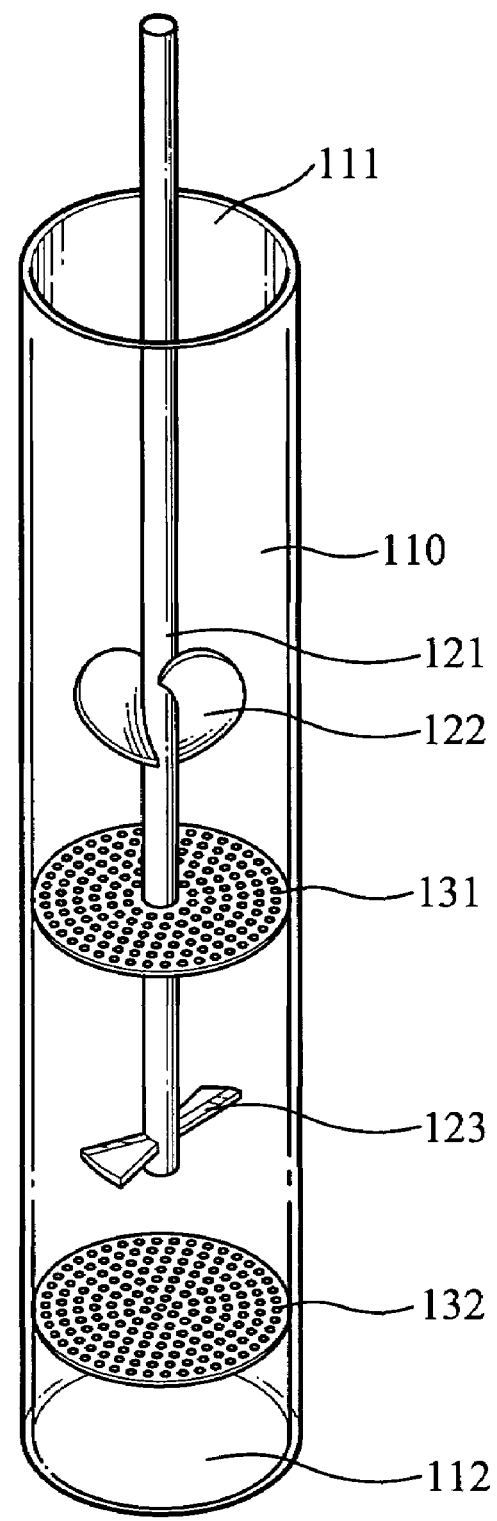
FIG. 1 shows the main structure of the tissue homogenizer of the present invention.

FIG. 1 shows the main structure of the tissue homogenizer 100 of the present invention comprising a first chamber 110, a driving mechanism 121, a pair of vanes (directing mechanism) 122, a pair of blades 123, a first filter 131 and a second filter 132. The first chamber 110 has a first opening 111 and a second opening 112. The driving mechanism 121 extends into the first chamber 110 from the first opening 111. The vanes 122 and the blades 123 are disposed on the driving mechanism 121 in the first chamber 110. The first filter 131 is disposed between the vanes 122 and the blades 123. The second filter 132 is disposed between the second opening 112 and the blades 123.

Figure 2:
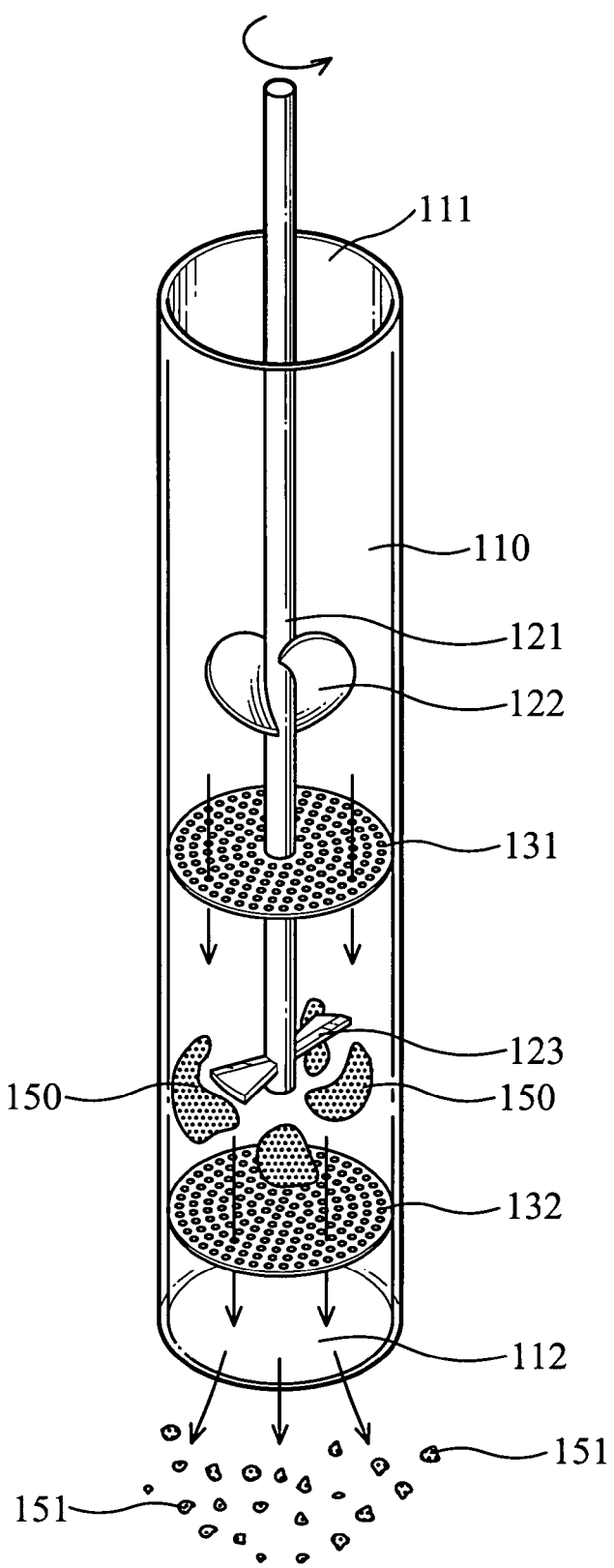
FIG. 2 shows homogenization of tissue pieces.

FIG. 2 shows the tissue homogenizer 100 homogenizing tissue pieces 150. The tissue pieces 150 are disposed between the first filter 131 and the second filter 132. The first filter 131 restricts the distribution of the tissue pieces 150. The first chamber 110 is filled with a fluid. The driving mechanism 121 is rotated to drive the vanes 122 and the blades 123. The blades 123 cut the tissue pieces 150. The vanes 122 impel the fluid from the first filter 131 to the second filter 132. The fluid moves the cut tissue pieces filtered by the second filter 132 generating homogenized tissue pieces 151.

The first filter 131 can be omitted to simplify the present invention, wherein distribution of the tissue pieces 150 is restricted by the first chamber 110.

Figure 3:
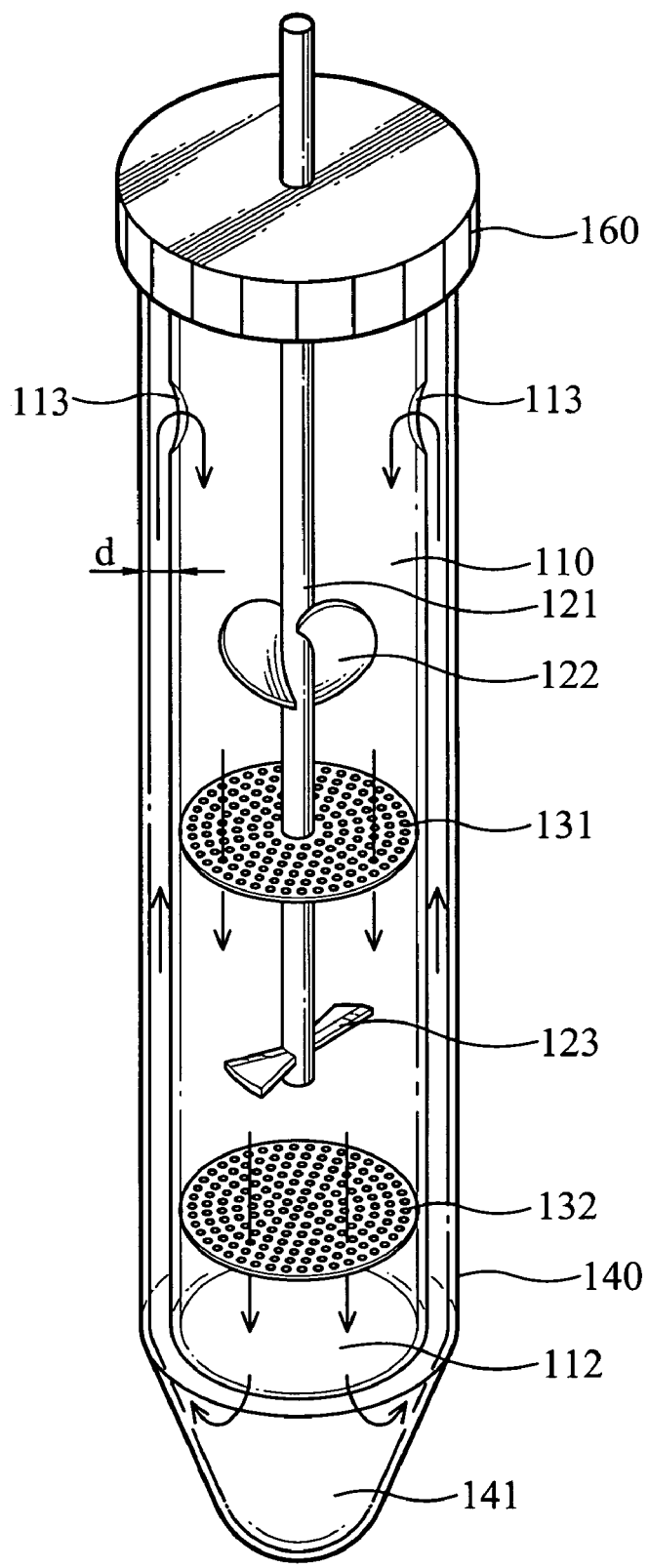
FIG. 3 shows the complete tissue homogenizer of the present invention.

FIG. 3 shows the complete tissue homogenizer, further comprising a second chamber 140 with a containing portion 141. The containing portion 141 is conical and disposed at an end of the second chamber 140. The first chamber 110 is disposed in the second chamber 140 at an interstice d from the inner wall thereof. Additionally, the first chamber 110 further comprises third openings 113. The fluid flows from the second opening 112, along the interstice d, and back to the first chamber 110 through the third openings 113. A lid 160 seals the first opening 111 and the second chamber 140 to limit the flow of the fluid.

Figure 4:
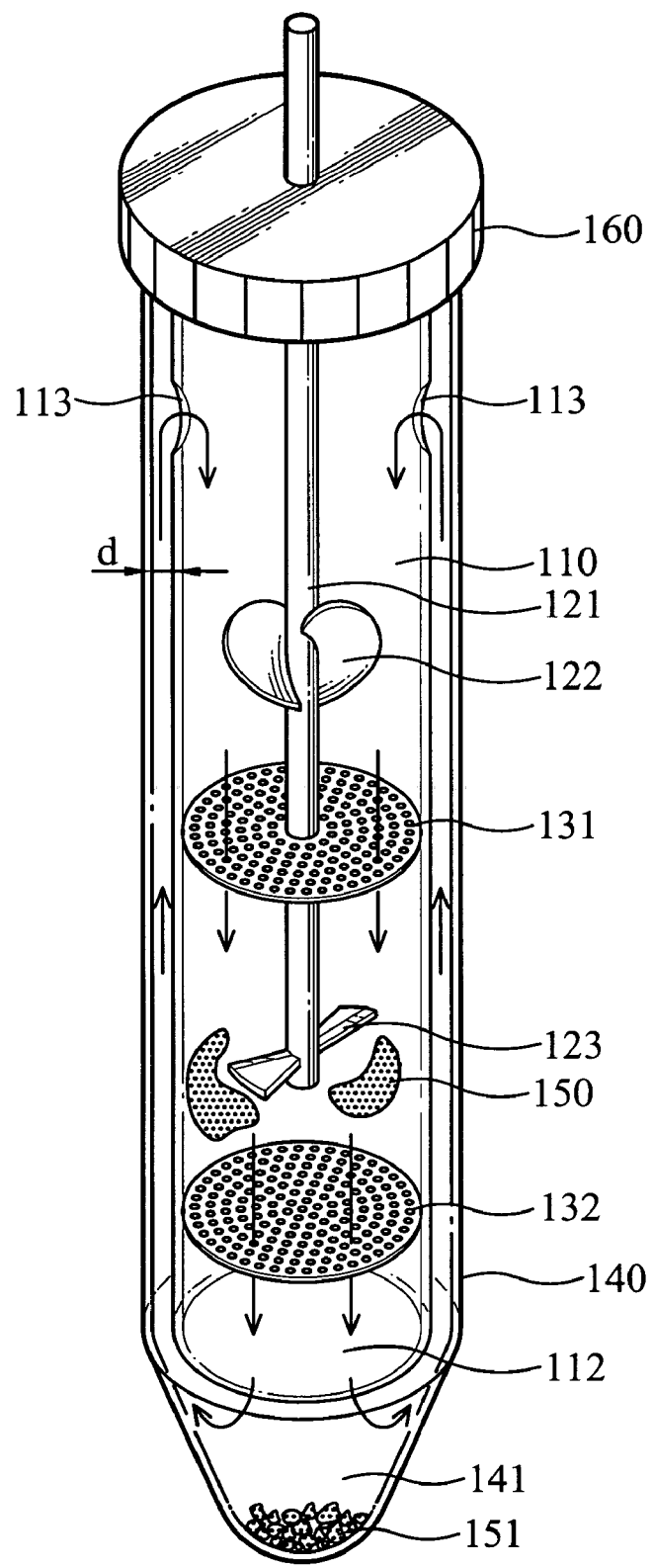
FIG. 4 shows the complete tissue homogenizer homogenizing tissue pieces.

In FIG. 4, homogenized tissue pieces 151 are impelled by the fluid through the second opening 112 and contained in the containing portion 141. The fluid circulates from the second opening 112 to the first chamber 110 through the third opening 113 along the interstice d. The fluid is directed by vanes 122. Thus, the fluid is recycled.

The width of the interstice d is smaller than the homogenized tissue pieces 151 to prevent reflux into the first chamber 110.

The second chamber 140 is a centrifuge tube. The fluid is culture medium. The homogenized tissue pieces 151 provide live histiocytes.

The present invention can also receive fluid directly into the first opening 111 to direct the homogenized tissue pieces 151. Additionally, the second chamber can be replaced by a third filter with through holes smaller than the second filter 132 to gather homogenized tissue pieces 151.

The present invention successively cuts, filters, and collects finally the homogenized tissue pieces in a sealed device. The present invention produces homogenized tissue pieces at lower cost in a shorter time, and prevents tissue waste. As well, because the present invention homogenizes the tissue piece by cutting, histiocytes are undamaged and can be applied in live histiocyte culture. Additionally, the present invention provides precise control of homogenized tissue piece by size the filter.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A tissue homogenizer, comprising:
   a first chamber, comprising a first opening and a second opening;
   a blade, disposed in the first chamber;
   a first filter, disposed in the first chamber between the first opening and the blade: and
   a second filter, disposed in the first chamber between the second opening and the blade,
   wherein a tissue piece placed in the first chamber is cut by the blade, and a fluid moves a plurality of cut tissue pieces through the second filter to produce a plurality of homogenized tissue pieces.

2. The tissue homogenizer as claimed in claim 1, further comprising a second chamber, comprising a containing portion, with the first chamber disposed therein, wherein the homogenized tissue pieces are impelled by the fluid through the second opening and contained in the containing portion.

3. The tissue homogenizer as claimed in claim 2, wherein the containing portion is a conical.

4. The tissue homogenizer as claimed in claim 2, wherein the first chamber further comprises a third opening, an interstice is formed between the first chamber and an inner wall of the second chamber, and the fluid circulates from the second opening to the first chamber through the third opening along the interstice.

5. The tissue homogenizer as claimed in claim 4, wherein the interstice is narrower than the size of the homogenized tissue pieces.

6. The tissue homogenizer as claimed in claim 2, further comprising a lid and sealing the first opening and the second chamber to limit the flow of the fluid.

7. The tissue homogenizer as claimed in claim 2, wherein the second chamber is a centrifuge tube.

8. The tissue homogenizer as claimed in claim 1, further comprising a driving mechanism, connected to the blade and driving the blade to cut tissue pieces.

9. The tissue homogenizer as claimed in claim 8, wherein the driving mechanism rotates the blade to cut the tissue piece.

10. The tissue homogenizer as claimed in claim 8, wherein the driving mechanism has a directing mechanism, disposed on the driving mechanism to direct the fluid.

11. The tissue homogenizer as claimed in claim 10, wherein the directing mechanism is a vane.

* * * * *